(12) United States Patent
Lasser et al.

(10) Patent No.: US 6,552,841 B1
(45) Date of Patent: Apr. 22, 2003

(54) ULTRASONIC IMAGER

(75) Inventors: Marvin E. Lasser, Potomac, MD (US); Robert S. Lasser, Washington, DC (US); John P. Kula, Columbia, MD (US)

(73) Assignee: Imperium Advanced Ultrasonic Imaging, Rockville, MD (US)

( * ) Notice: Subject to any disclaimer, the term of this patent is extended or adjusted under 35 U.S.C. 154(b) by 0 days.

(21) Appl. No.: 09/479,598

(22) Filed: Jan. 7, 2000

(51) Int. Cl.[7] .......................... G02F 1/33; G03B 42/06; A61B 8/14
(52) U.S. Cl. .......................... 359/305; 367/7; 600/437; 600/447
(58) Field of Search ................... 359/305, 285, 359/311, 312, 322, 323; 367/7; 600/437, 447

(56) References Cited

U.S. PATENT DOCUMENTS

| | | |
|---|---|---|
| 3,711,823 A | * 1/1973 | Green .................. 367/7 |
| 3,918,297 A | * 11/1975 | Rocha .................. 73/607 |
| 3,927,557 A | * 12/1975 | Viertl .................. 73/67.5 R |
| 4,001,766 A | 1/1977 | Hurwitz |
| 4,194,510 A | 3/1980 | Proudian |
| 4,305,296 A | 12/1981 | Green et al. |
| 4,434,662 A | 3/1984 | Green |
| 4,452,083 A | * 6/1984 | Brettel et al. ............ 73/607 |
| 4,506,550 A | * 3/1985 | Sandhu .................. 73/603 |
| 4,933,560 A | 6/1990 | Messiou et al. |
| 4,949,310 A | 8/1990 | Smith et al. |
| 5,058,250 A | 10/1991 | Turnbull |
| 5,087,816 A | 2/1992 | Robin et al. |
| 5,160,870 A | 11/1992 | Carson et al. |
| 5,179,455 A | 1/1993 | Garlick |
| 5,212,571 A | 5/1993 | Garlick et al. |
| 5,235,553 A | 8/1993 | Garlick et al. |
| 5,240,005 A | 8/1993 | Viebach |
| 5,283,438 A | 2/1994 | Dautriche |
| 5,329,817 A | 7/1994 | Garlick et al. |
| 5,406,163 A | 4/1995 | Carson et al. |
| 5,446,334 A | 8/1995 | Gaffney |
| 5,483,963 A | 1/1996 | Butler et al. |
| 5,488,954 A | 2/1996 | Sleva et al. |
| 5,502,307 A | 3/1996 | Baliga et al. |
| 5,577,507 A | 11/1996 | Snyder et al. |
| 5,620,740 A | 4/1997 | Baliga et al. |
| 5,653,235 A | 8/1997 | Teo |
| 5,655,537 A | 8/1997 | Crowley |
| 5,689,576 A | 11/1997 | Schneider et al. |
| 5,747,117 A | 5/1998 | Dannenberg |
| 5,751,059 A | 5/1998 | Prost |
| 5,776,068 A | 7/1998 | Silverman et al. |
| 6,159,149 A | 12/2000 | Erikson et al. |

* cited by examiner

*Primary Examiner*—Hung Xuan Dang
*Assistant Examiner*—Tuyen Tra
(74) *Attorney, Agent, or Firm*—Burns, Doane, Swecker & Mathis, LLP

(57) ABSTRACT

An imaging system is disclosed which can provide images of received acoustic energy. In one embodiment, a transducer emits an acoustic beam which is reflected off of an acoustic beam splitter onto a target. The acoustic beam then reflects off of the target and is received by a piezoelectric imaging array which converts the acoustic beam into electrical signals. In another embodiment, a transducer transmits an acoustic beam through a target before being received by the piezoelectric imaging array on the opposite side of the target. In both embodiments, an acoustic lens system is disposed between the target and the imaging array to permit the system to focus upon, and magnify, features of interest within the target.

33 Claims, 7 Drawing Sheets

ULTRASONIC IMAGER

BACKGROUND

The present invention relates generally to acoustic imaging and, more specifically, to systems and methods for acoustic imaging.

Acoustic imaging has been conventionally used in various material testing or measurement applications. For example, ultrasonic imaging has been used in non-destructive testing applications such as the testing of the properties of manufactured materials (e.g., testing for corrosion in aircraft wings). Ultrasonic imaging has further been used in medical imaging applications such as human soft tissue diagnosis. Conventional systems used to perform ultrasonic testing suffer from a number of disadvantages, such as system complexity and lack of image resolution.

U.S. Pat. No. 5,212,571 to Garlick et al., the disclosure of which is hereby incorporated by reference in its entirety, discloses an acoustic imaging system that includes an ultrasonic transducer which generates plane waves through a deformable membrane and into one side of an object. Another deformable membrane contacts the other side of the object, for coupling ultrasonic energy passing through the object into a container that contains a liquid coupling medium. Ultrasonic plane waves are directed through the liquid coupling medium to a liquid/gas interface surface of the liquid coupling medium, referred to as a hologram detection surface. A coherent light beam from a laser is used to illuminate the hologram detector surface to generate a diffracted optical image that is filtered and supplied to a viewing lens. Thus, the Garlick patent discloses use of a complex acoustic imaging device which uses laser illumination of a single liquid/gas interface to produce an object image. It would be desirable to provide an acoustic imaging system which can be implemented in a compact, cost effective manner, which achieves high image resolution without detrimental speckle noise, and which avoids the complex configuration of systems such as that disclosed by Garlick.

SUMMARY

The present invention is directed to reduction and/or elimination of speckle noise and other undesirable characteristics associated with acoustic imaging, while maintaining and/or improving the image resolution achieved by a compact, cost-effective system.

Exemplary embodiments of the invention relate to methods and systems for acoustic imaging. An exemplary acoustic imaging system comprises: a first transducer for generating an unfocused acoustic beam and for directing the unfocused acoustic beam into a target; and an acoustic lens system for focusing a portion of the acoustic beam received from the target onto an imaging array, said imaging array comprising a two dimensional array of acoustic to electrical transducers which produce electrical signals in response to the portion of the acoustic beam received by the imaging array. Speckle noise reduction is accomplished, at least in part, via combination of the unfocused acoustic beam, the acoustic lens and the two dimensional imaging array, by which an incoherent beam received from a target is focused onto the surface of a two-dimensional imaging array or discrete acoustic to electrical transducer.

In one exemplary embodiment, a portion of the acoustic beam transmitted through at least a portion of the target is received by the acoustic lens (transmission mode).

In alternate embodiments, a portion of the acoustic beam reflected from the target is received by the acoustic lens (reflection mode).

Exemplary embodiments also include an imaging array having a semiconductor material upon which the piezoelectric material is formed.

Exemplary embodiments can be implemented in a cost-effective and compact manner suitable, for example, as a hand-held device.

In alternate embodiments, an interface is provided for the acoustic imaging array, the interface being a solid material that is transmissive to acoustic energy, and that is placed in contact with an exposed surface of the imaging array to couple acoustic energy onto the imaging array.

BRIEF DESCRIPTION OF THE DRAWINGS

The objects and advantages of the invention will be understood by reading the following detailed description in conjunction with the drawings in which.

DETAILED DESCRIPTION OF PREFERRED EMBODIMENTS

Figure 1:
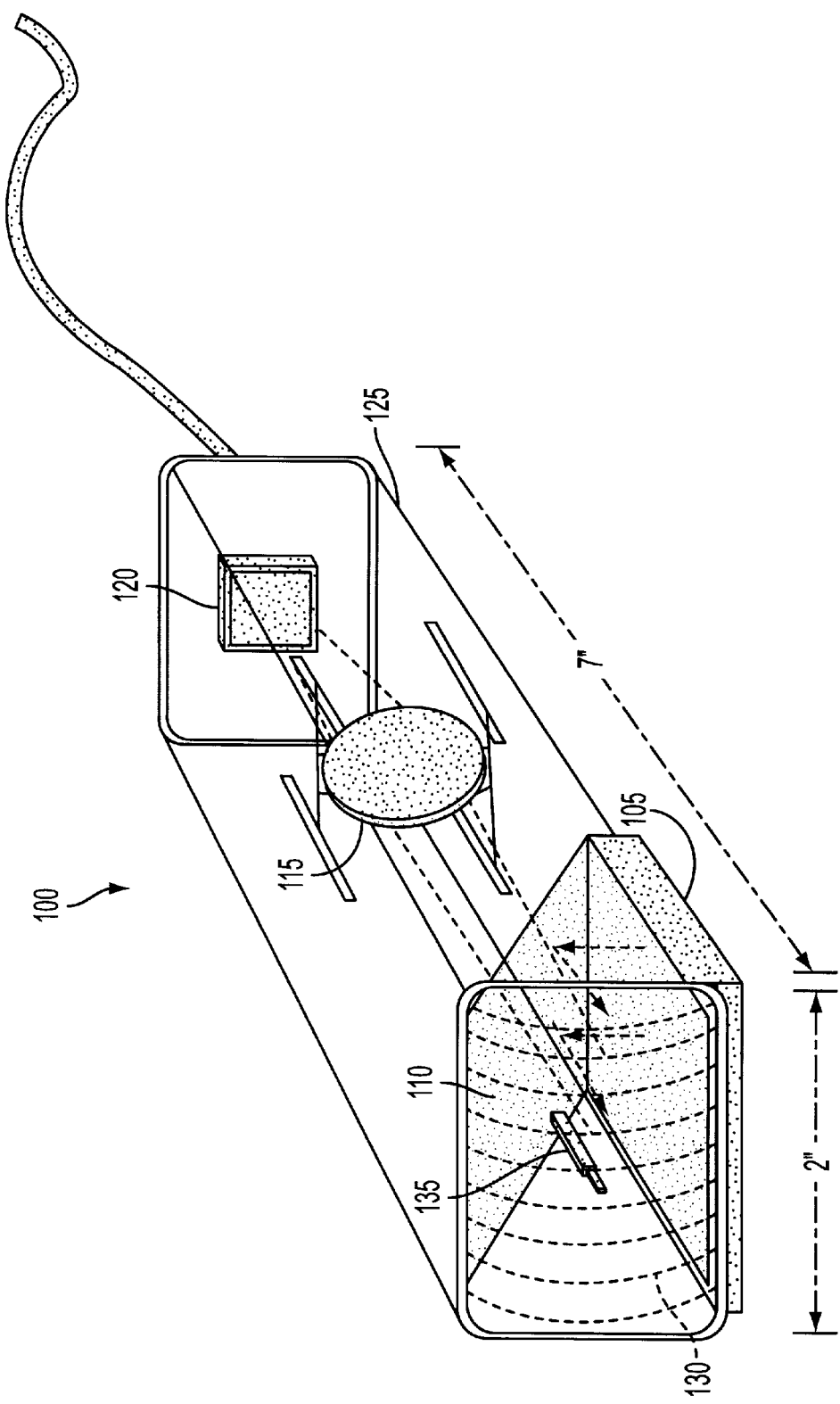
FIG. 1 is a structural diagram of an ultrasonic device, in accordance with an exemplary embodiment of the invention, which images acoustic energy reflected from a target of interest.
Figure 2:
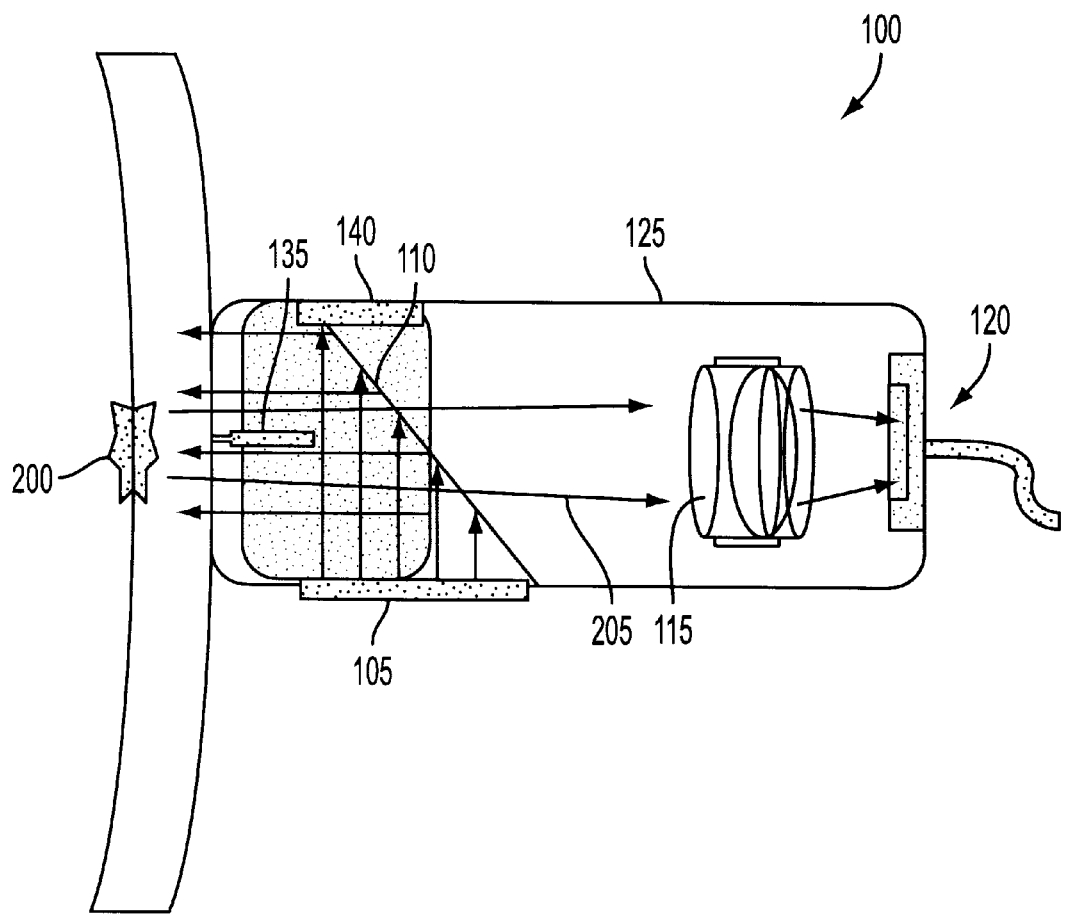
FIG. 2 is another view of the exemplary FIG. 1 embodiment.

FIGS. 1 and 2 illustrate a system configuration that permits measurement of acoustic energy which is reflected from a target ("reflection mode"). The device 100 of this exemplary embodiment comprises a flat source acoustic transducer 105, an acoustic beam splitter 110, an acoustic lens 115 of an acoustic lens system, and an imaging array 120 contained in a probe housing 125. The inside volume of the housing 125 is additionally filled with a fluid, such as water, which is transmissive to acoustic energy.

In operation, the flat source acoustic transducer 105 generates an unfocused acoustic beam that can be directed into a target material for diagnostic testing. Where the housing is dimensioned to be hand-held, the acoustic transducer could be approximately one inch square, though any other desired size may be appropriate for different dimensions of the housing 125 can be selected. As one skilled in the art will appreciate, acoustic transducers which can generate a sufficiently uniform beam are known in the art and need not be discussed in detail.

The beam generated from the transducer 105 impacts the acoustic beam splitter 110, where the beam is split such that any desired fraction of the beam is reflected off the beam splitter 110 and out through a target couplant 130. The target couplant 130 is formed to encompass the face of the housing 125 and is comprised of a material such as latex. Other materials, however, can be selected for the target couplant 130 provided the selected material is deemed sufficiently pliable to, for example, permit coupling of the housing with a curved target surface, and provided the properties of the material permit transmission of acoustic energy.

The acoustic beam splitter 110 can be of any known type, including but not limited to those composed of a material that has an acoustic impedance mismatch with the surrounding media (e.g., water). Due to the acoustic impedance mismatch, the material of the beam splitter 110 reflects a portion of the acoustic beam transversely while transmitting a portion of the beam so that it propagates axially. The thickness of the material of the beam splitter 110 can be selected such that the thickness is greater than one half of a wavelength of the acoustic beam to ensure a sufficient acoustic mismatch, although any material thickness deemed acceptable for a particular application can be used. In one exemplary embodiment, the thickness of the beam splitter 110 is selected such that the ratio of the transverse reflected beam to the axial transmitted beam is approximately 50%. However, any desired ratio deemed acceptable can be used. Examples of materials that can be used in beam splitter 110 include a thin sheet of glass or a thin sheet of metal, such as aluminum or steel. However, one skilled in the art will recognize that other suitable beam splitting materials can also be used.

As shown in FIG. 2, an acoustic reflective surface 140 can additionally be positioned within the probe housing 125 directly across from the transducer 105. This reflective surface 140 will reflect energy that has been transmitted from the transducer 105 through the acoustic beam splitter 110 to a target 200, from where it will be reflected onto the array 120. The beam will be coincident with the beam that is reflected from the target and thus a doppler signal will be generated if there is any movement within the target normal to the beam that is incident on the target.

The beam from the transducer 105 that is reflected off the beam splitter 110 propagates out through the target couplant 130 and into the target material 200 (FIG. 2). The portion 205 of the beam which reflects normally off of the target material then propagates back through the beam splitter 110 and through the acoustic lens 115. Acoustic lenses are well known in the art and, in accordance with the present invention, can be constructed of any materials, and in any configuration, appropriate for the specific device housing size, acoustic beam wavelength, and fluid medium (e.g., water) that is selected. The acoustic lens 115 is located within housing 125 such that the lens focuses the acoustic beam onto the imaging array 120 comprising, for example, a piezoelectric material which produces electrical signals in response to a portion of the acoustic beam received by the imaging array. That is, acoustic energy incident on the piezoelectric material is converted into electrical signals that can be processed by any subsequent associated circuitry and conventional image processing hardware and/or software (not shown). Such image processing hardware and/or software can include conventional data acquisition, digital signal processing, and video/graphics hardware and/or software, such as that disclosed in U.S. Pat. No. 5,483,963, the disclosure of which is incorporated herein in its entirety.

Figure 9:
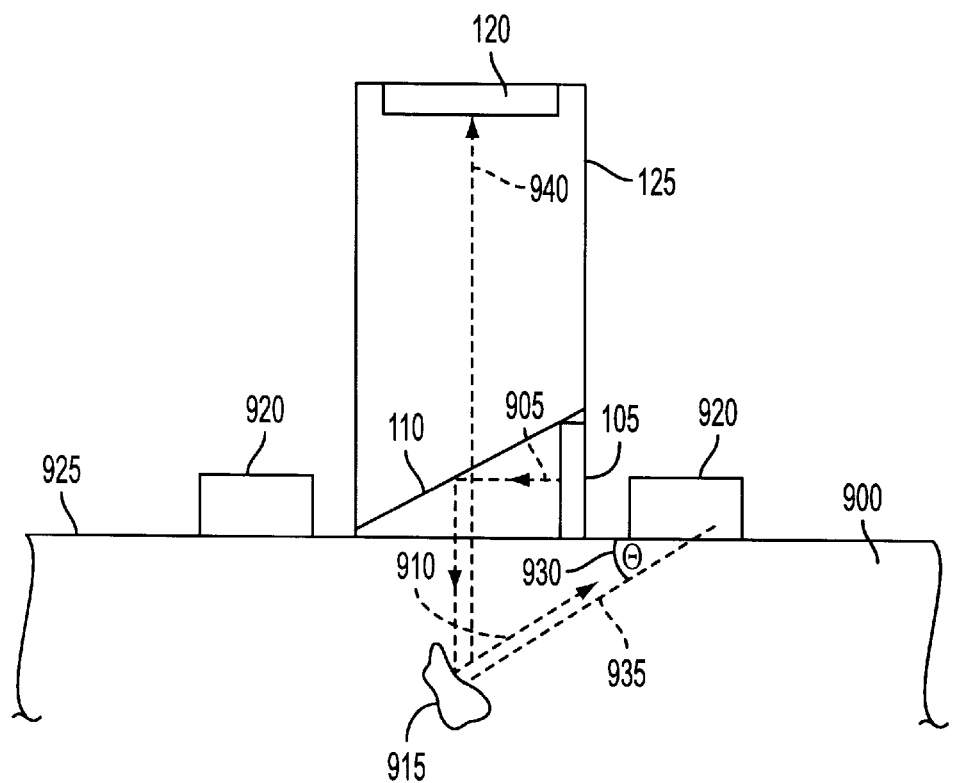
FIG. 9 illustrates "reflection mode" imaging using additional transducers in accordance with an additional embodiment of the present invention.

FIG. 9 illustrates a variation of the "reflection mode" acoustic imaging process described above with respect to FIGS. 1 and 2. In normal "reflection mode," imaging of features within a target material 900 requires that the features reflect incident acoustic energy at an angle with respect to the incident beam such that the reflected beam is directed back onto the imaging array 120. As shown in FIG. 9, an acoustic beam 905 from transducer 105 may reflect in a direction 910 that prevents the beam from reaching the imaging array 120 when the feature 915 is not oriented normal to the incident acoustic beam. One embodiment of the present invention therefore uses one or more additional transducers 920, placed adjacent to the housing 125, to direct acoustic energy into the target 900 at an angle (θ) 930 which will ensure that a feature not oriented normal to the incident acoustic beam 935 will reflect the incident beam along a path 940 onto the imaging array 120. Though beam splitter 110 is shown as being used in FIG. 9, transducers 920 can be used alone in the illustrated configuration (i.e., no beam splitter or transducer required within housing 125) to direct acoustic beams into the target for reflection back onto the array 120.

Figure 3:
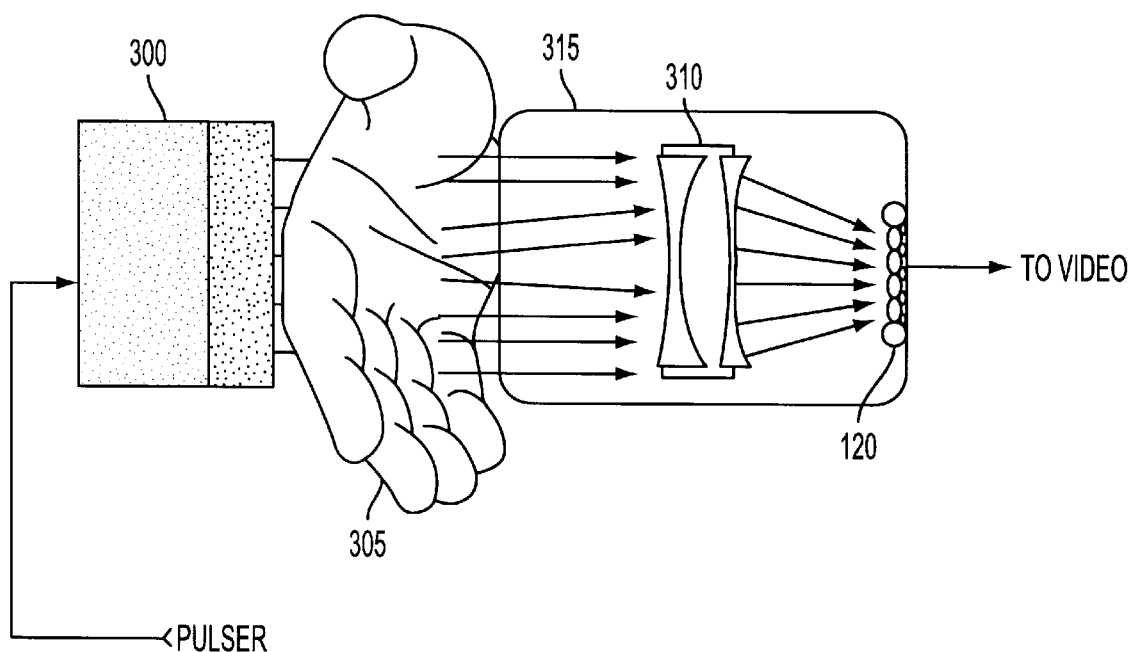
FIG. 3 is a diagram of an ultrasonic device, in accordance with an exemplary embodiment of the invention, which images acoustic energy transmitted through a target of interest.

A second exemplary embodiment of the invention is configured as a system to operate in a "transmission mode." As shown in FIG. 3, a large unfocused acoustic transducer 300 is placed on one side of a target 305, and a housing 315 containing an acoustic lens system 310 and imaging array 120 is placed on the opposite side of the target 305, and in line with transducer 300. Acoustic lens 310 focuses the portion of the acoustic beam, which is transmitted through the target 305, onto the imaging array 120. Similar to the target couplant 130 described with respect to FIG. 1, target couplant material (not shown in FIG. 3) can be formed over both the emissive surface of acoustic transducer 300 and the receiving surface of housing 315 to couple acoustic energy from the transducer into the target 305 and onto the array 120.

Operation of this exemplary embodiment in "transmission mode" can be advantageous in diagnostic testing since it is not necessary for the region being tested to be oriented normal to the incident ultrasonic beam. In medical diagnostic testing, tissue features have varying degrees of absorptivity and reflectivity at any given orientation, and therefore a system which relies on reflected acoustic energy may miss important tissue features. In "transmission mode," the image is formed by absorption of the transmitted ultrasound beam, as well as reflection of the ultrasound beam, and thus features which may not have reflected the incident beam in the proper direction can still be detected.

The exemplary embodiment illustrated in FIG. 1 shows the use of a single acoustic lens for focusing the acoustic beam onto the imaging array 120. However, a multi-lens system can be used with any of the exemplary embodiments of the present invention. For example, a three lens system can be used in accordance with known acoustic principles. As is known in the art, the acoustic magnification provided by a lens is determined by the focal length of the lens as related by the lens equation:

$$\frac{1}{u} + \frac{1}{v} = \frac{1}{f}$$

where
  u is the object distance;
  v is the image distance; and
  f is the focal length.

Since the magnitude of the magnification M provided by the lens is the ratio of object to image distance, a variation in focal length will vary the magnification M. The zoom lens of an exemplary embodiment of the present invention incorporates three lenses, a first positive lens, a second negative lens, and a third positive lens. The first and second lenses are of equal and opposite power. The range ($EFL_{max}$–$EFL_{min}$) of the effective focal length (EFL) of the first two lenses is given by the following relations:

$$EFL_{min} = \frac{f_a f_b}{(f_a + f_b)}$$

$$EFL_{max} = \frac{2 f_a f_b}{(f_a + 2 f_b)}$$

where $f_a$ is the focal length of the positive lens; and $f_b$ is the focal length of the negative lens When the separation between the two lenses is zero, EFL reaches $EFL_{max}$. EFL, however, decreases as the distance between the lenses increases. $EFL_{min}$ is reached when the distance between the lenses approaches the focal length of the first positive lens. The third lens in the three lens system is also a positive lens that uses the virtual image formed by the first two lenses as an object and then collimates the diverging rays to form an image upon the imaging array 120. The lens therefore includes a negative lens located between two positive lenses. Axial movement of the center negative lens varies the power of the zoom lens system. Though an exemplary three lens system is described, one skilled in the art will appreciate that other lens arrangements can be used in accordance with conventional acoustic principles.

Figure 4:
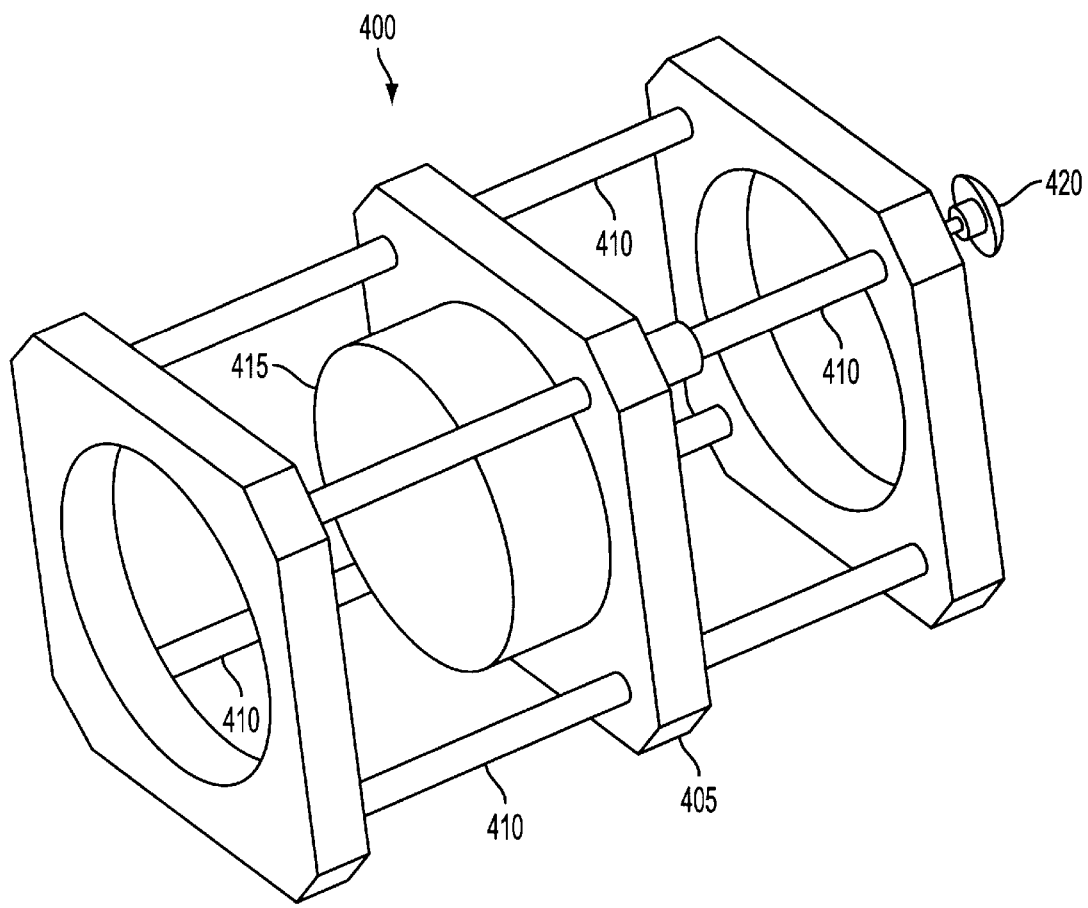
FIG. 4 is a structural diagram of a lens position adjustment system in accordance with an exemplary embodiment of the invention.

Adjustment of a position of the multi-lens system to provide focus can be achieved in a number of ways. FIG. 4 illustrates one exemplary lens positioning system 400 in which the lens 115 (FIG. 1) is mounted within an orifice 415 in a central plate 405 that slides upon precision rails 410. In this embodiment, adjustment of a lead screw 420 with beveled gears provides the movement of the central plate 405 containing the lens 310. Lens positioning system 400 therefore permits different depths in the target to be focused upon depending on the position of the central plate 405. One skilled in the art will recognize that other means for moving the central plate can also be used, including a motor driven central plate 405 with associated electronic control circuitry.

Figure 5:
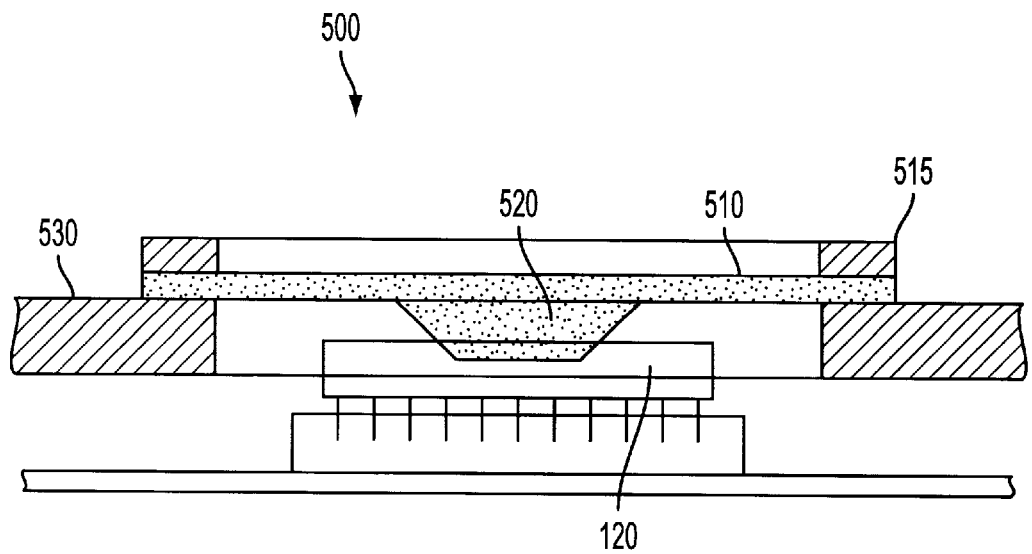
FIG. 5 illustrates an exemplary array interface for coupling acoustic energy onto the imaging array.

The focused acoustic beam from acoustic lens 115 or 310 of the exemplary embodiments shown in FIG. 1, 2 or 3, can be optionally coupled onto the imaging array 120 through an array interface 500, such as that shown in FIG. 5. Array interface 500 comprises a diaphragm 510, a retainer ring 515, and a pyramid 520. Diaphragm 510 is sealed to a backplate 530 of the probe using retainer ring 515. The diaphragm 510 can be comprised of a solid material, such as AQUALENE™ (available from Materials Research Institute of Ontario, Canada) or polyurethane, which transmits acoustic energy, but which prevents the fluid media filling the probe housing 125 (FIG. 1) from contacting the imaging array 120. The pyramid 520 of acoustically transmissive material contacts both the diaphragm 510 and the surface of the array 120. The array interface 500 therefore couples acoustic energy from the fluid media across the diaphragm 510 and the pyramid 520 and onto the array 120.

Imaging array 120, shown in FIGS. 1 and 3, can include any number of piezoelectric arrays that are known in the art. The array of PZT detectors described in U.S. Pat. No. 5,483,963, the disclosure of which is hereby incorporated by reference in its entirety, can be used for example. As additional examples, the arrays of piezoelectric polyvinylidene difluoride (PVDF) polymers described in U.S. Pat. Nos. 5,406,163 or 5,283,438, the disclosures of which are hereby incorporated by reference in their entirety, can also be used.

Figure 6:
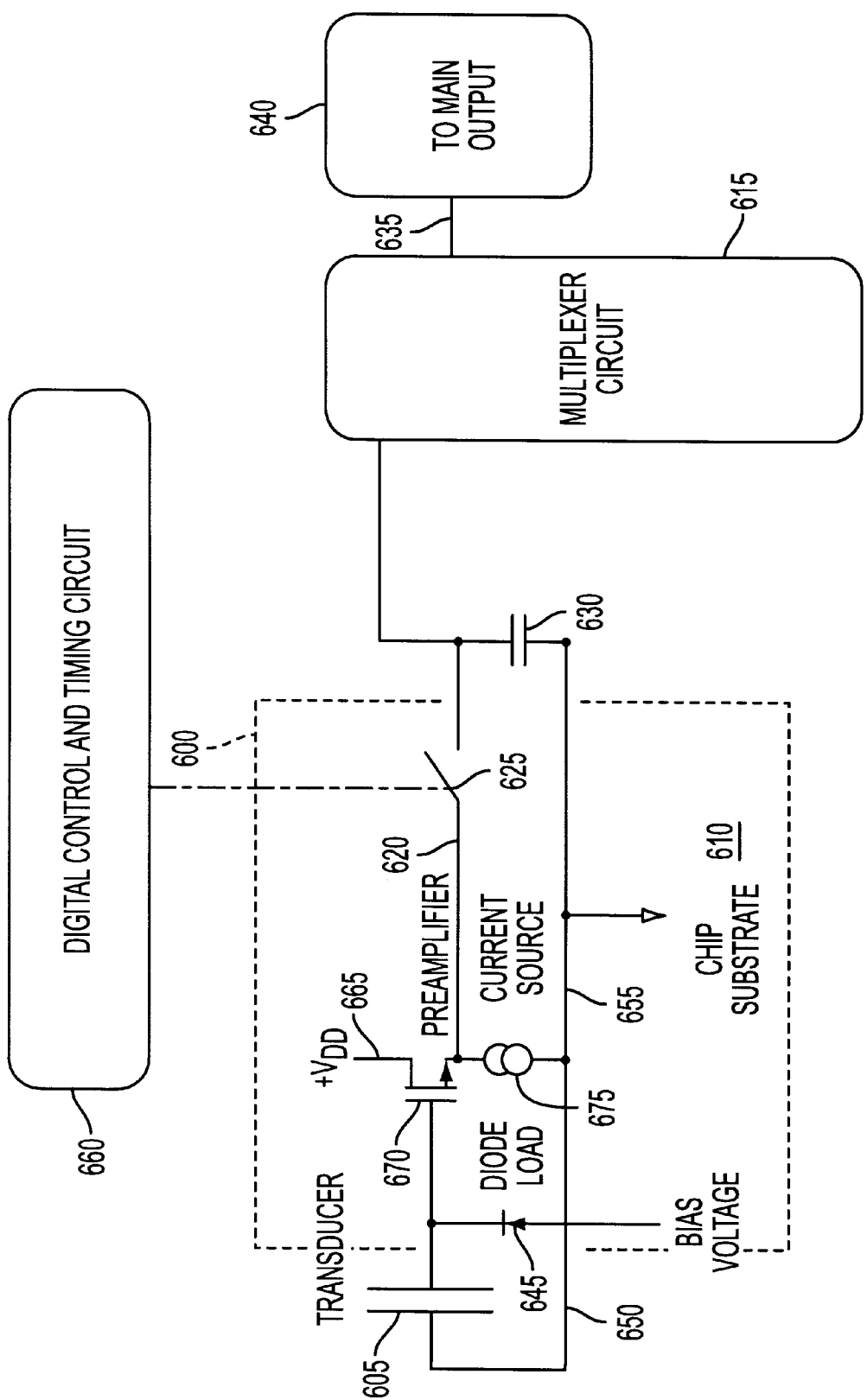
FIG. 6 is a schematic diagram of an exemplary read-out integrated circuit of the present invention.

An exemplary read out integrated circuit (ROIC) for sampling the output from each piezoelectric element (piezel) of the imaging array 120 is shown in FIG. 6. Of course, rather than configuring the read out device as an integrated circuit, discrete components can be used. Each piezel 605 has an associated input circuit 600 embodied, for example, in a semiconductor substrate 610. Input circuit 600 is digitally controlled and timed to supply sampled inputs via a multiplexer circuit 615 to a main output 640. The sample and hold circuit is configured as a switch 625, capacitor 630 and is controlled by an associated digital control and timing circuit 660 which can be configured in conventional fashion (e.g., programmable microprocessor) to adjust the hold time of the sample and hold circuit as desired (for example, for 0.5 microseconds, or longer or shorter, as desired). Input circuit 600 has a preamplifier 670 which is biased with biasing voltage $V_{DD}$ 665. A current source 675 provides line 620 with a signal which is also coupled to the output of the preamplifier 670. The preamplifier 670 amplifies the signal from the piezel 605. A load diode 645 is connected across the output of the piezel 605 and the bias voltage 650. Integrated circuit chip substrate 655 is connected to one side of the current source 675. Sample and hold capacitor 630 samples and holds the output from the preamplifier 670 for various timing periods when switch 625 is closed in response to a control signal from the digital control & timing circuit 660.

Preamplifier 670 buffers the piezel impedance to drive the sample and hold switch 625. The load diode 645 controls the DC voltage at the preamplifier 670 input. The digital control and timing circuit 660 controls the opening and closing of switch 625. Multiplexer 615 is provided to multiplex the output of each of the piezels in the imaging array to a multiplexed output 635. Multiplexed output 635 is input into the main output 640 along with sampled outputs associated with other piezels in the imaging array.

Exemplary embodiments can be implemented in both continuous wave and/or in pulse modes for both transmission and reflective modes. For example, pulse modes operating with range gating can be used to examine a "slice" of a target in a reflective mode, or can be used to examine a specified target depth in a transmissive mode.

Figure 7:
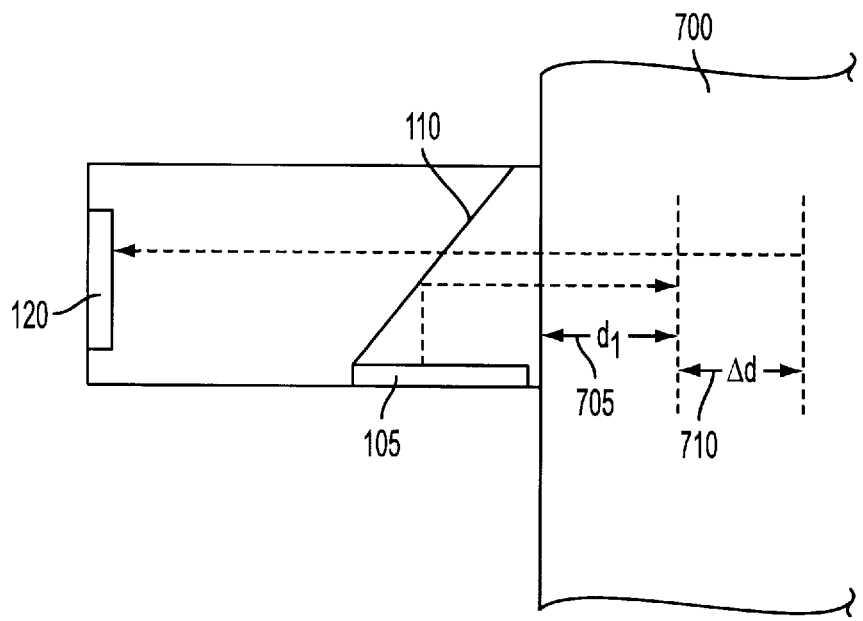
FIG. 7 illustrates the use of "range gating" to image at given depths within a target material.
Figure 8:
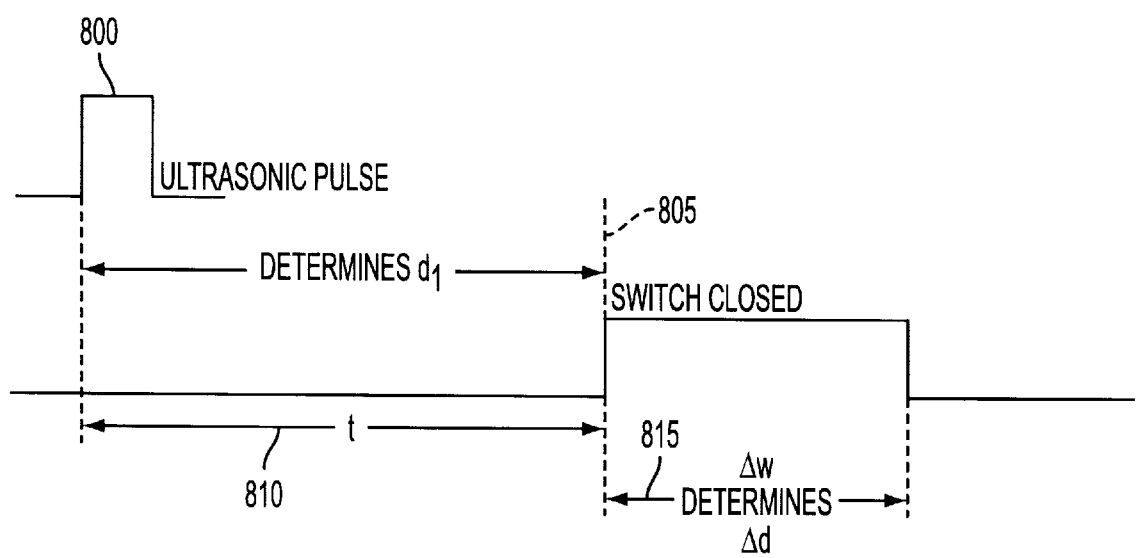
FIG. 8 illustrates a timing diagram for opening and closing of the sample and hold switch in accordance with the "range gating" of FIG. 7.

The digital control and timing circuit 660 can be used in conjunction with input circuit 600 to "range gate" the acoustic beam that is received at the imaging array 120 and output from piezoelectric transducer 605. "Range gating" is the process of controlling two parameters: 1) the time t (810; FIG. 8) between the acoustic pulse (800; FIG. 8) at transducer 105 and the time (805; FIG. 8) at which switch 625 is closed to begin sampling; and 2) the duration Δw (815; FIG. 8) over which switch 625 is closed. The control of the timing of when switch 625 is closed determines the initial depth $d_1$ within the target (705; FIG. 7) at which the imaging array begins sampling. Control of the duration Δw of the closing of the switch 625 determines the depth Δd (710; FIG. 7) of the target over which the imaging array receives the acoustic energy from the target and thus the "slice" of the target which is imaged.

A further exemplary embodiment of the invention implements a depth finder that advantageously permits the user to determine the depth of a target of interest below the surface of the material being tested. This depth finding function can be performed by emitting a short pulse from a transducer and measuring the time of travel from pulse emission until the pulse reaches the imaging array. A conventional off-the-shelf pulse echo device 135 can be used to perform this function. Use of such a conventional pulse echo device permits the detection of distances with an accuracy within a small fraction of a millimeter, without having to modify the array processing circuitry.

The exemplary embodiment of FIG. 3 can be used in numerous applications, including the medical diagnosis of human tissue. Using the focus and zoom capabilities of the present invention, the entire depth of human tissue can be scanned. These capabilities are particularly advantageous in breast tissue analysis, where the layers of tissue surrounding a breast mass can be separated. Thus, spiculated borders, which are indicative of malignancy of the breast, can more readily be detected. The present invention also provides advantages for guiding core biopsy, cyst drainage and percutaneous tumor ablation. The exemplary embodiment of FIG. 3 additionally can be used to assess the tendons and vessels in the body, such as those of the hands or wrists. The present invention provides delineation of tendons and the bony structures of the fingers and has sufficient penetration of the bones and the fingers that it is feasible to monitor the placement of surgical pins, in real-time, without x-rays.

The exemplary embodiment illustrated in FIG. 1, operating in "reflection mode," is useful for the non-invasive imaging of objects located under layers of material. Voids, corrosion, delaminations, impact damage, and subsurface cracking are a few of the structural features that can be imaged within a material. The exemplary embodiment of FIG. 1 permits the testing of materials with large surface areas, such as large composite or metal sheets, in a fraction of the time of conventional slower C-scan ultrasound systems. For example, typical C-scan testing of a 100 square foot material can require 6096 passes over a period of 16.9 hours assuming a minimum spatial resolution of 0.5 mm and a scanning rate of 12 inches per second. However, with the same resolution and scanning rate, the exemplary embodiment of FIG. 1 can cover 100 square feet or more with only 48 passes or less in 8 minutes or less. The present invention thus offers several orders of magnitude improvement in the speed of testing over conventional ultrasonic imagers.

The exemplary embodiment of FIG. 1 can additionally be used for underwater detection and identification of mines, subsurface ship salvage, and high resolution imaging in the littoral zone with high resolution. This is in marked contrast to conventional ultrasound side scanning techniques which can detect objects in the ocean, but which have limited resolution. The integrated array, read-out circuitry, and standard video electronics, allows the overall device to be contained within a small package, thus permitting the device to be carried underwater by a diver. This capability to provide high resolution images from a hand-held ultrasonic device currently does not exist.

Although a number of embodiments are described herein for purposes of illustration, these embodiments are not meant to be limiting. Those of ordinary skill in the art will recognize modifications that can be made in the illustrated embodiment. Such modifications are meant to be covered by the spirit and scope of the appended claims.

What is claimed is:

1. An acoustic imaging system comprising:
   a first transducer for generating an unfocused acoustic beam, wherein the first transducer is arranged on one side of a target; and
   an acoustic lens system arranged on an opposite side of the target for focusing a portion of the acoustic beam received from the target onto an imaging array, said imaging array comprising a two dimensional array of acoustic to electrical transducers which produce electrical signals in response to the portion of the acoustic beam received by the imaging array.

2. The acoustic imaging system of claim 1, wherein an acoustic beam splitter receives the acoustic beam generated by the first transducer and directs a first portion of the acoustic beam into the target.

3. The acoustic imaging system of claim 2, wherein the beam splitter comprises a thin sheet of glass.

4. The acoustic imaging system of claim 2, wherein the beam splitter comprises a thin sheet of metal.

5. The acoustic imaging system of claim 4, wherein the thin sheet of metal comprises aluminum.

6. The acoustic imaging system of claim 4, wherein the thin sheet of metal comprises steel.

7. The acoustic imaging system of claim 1, further comprising:
   a second transducer that directs a second acoustic beam into the target.

8. The acoustic imaging system of claim 7, wherein a portion of the second acoustic beam is reflected from the target and received by the acoustic lens system.

9. The acoustic imaging system of claim 8, wherein the acoustic lens system focuses the portion of the second acoustic beam onto the array and wherein the array produces electrical signals responsive to the second acoustic beam.

10. The acoustic imaging system of claim 1, further comprising:
    means for processing the electrical signals from the array to produce image frames.

11. The acoustic imaging system of claim 10, further comprising:
    means for storing the image frames.

12. The acoustic imaging system of claim 10, further comprising:
    means for displaying the image frames.

13. The acoustic imaging system of claim 1, wherein the first transducer comprises a large area piezoelectric transducer.

14. The acoustic imaging system of claim 1, further comprising:
    means for adjusting a position of the acoustic lens system.

15. The acoustic imaging system of claim 14, wherein the means for adjusting the position of the acoustic lens system includes means for adjusting a focus of the acoustic lens system.

16. The acoustic imaging system of claim 14, wherein the means for adjusting the position of the acoustic lens system includes means for adjusting a magnification of the acoustic lens system.

17. The acoustic imaging system of claim 1, further comprising:
    a fluid medium for coupling the acoustic beam from the first transducer to a pliable material.

18. The acoustic imaging system of claim 17, wherein the pliable material couples the acoustic beam into the target.

19. The acoustic imaging system of claim 1, further comprising:
    means for determining a depth of a feature within said target.

20. The acoustic imaging system of claim 1, wherein the acoustic lens system focuses the portion of the acoustic beam received from the target directly onto the imaging array.

21. The acoustic imaging system of claim 1, further comprising a couplant disposed between the first transducer and the target.

22. The acoustic imaging system of claim 21, wherein the couplant is a pliable material transmissive to acoustic energy, the couplant encompassing a face of a housing for the first transducer.

23. A method of imaging a target using acoustic energy comprising:

generating an unfocused acoustic beam;

directing the unfocused acoustic beam into one side of a target;

focusing a portion of the acoustic beam received from an opposite side of the target onto a two dimensional imaging array comprising acoustic to electric transducers; and producing electrical signals responsive to the acoustic beam.

24. The method of claim 23, further comprising: coupling the unfocussed acoustic beam to the target with a pliable couplant.

25. An acoustic detector comprising:

an array comprising a piezoelectric material; and a solid material that is transmissive to acoustic energy, wherein the solid material is placed in contact with an exposed surface of the array to couple acoustic energy onto the array.

26. An acoustic imaging system comprising:

a first transducer for generating an unfocused acoustic beam and for directing the unfocused acoustic beam into a target; and an acoustic lens system for focusing a portion of the acoustic beam received from the target onto an imaging array, said imaging array comprising a two dimensional array of acoustic to electrical transducers which produce electrical signals in response to the portion of the acoustic beam received by the imaging array, wherein an acoustic beam splitter receives the acoustic beam generated by the first transducer and directs a first portion of the acoustic beam into the target.

27. The acoustic imaging system of claim 26, wherein the beam splitter comprises a thin sheet of glass.

28. The acoustic imaging system of claim 26, wherein the beam splitter comprises a thin sheet of metal.

29. The acoustic imaging system of claim 28, wherein the thin sheet of metal comprises aluminum.

30. The acoustic imaging system of claim 28, wherein the thin sheet of metal comprises steel.

31. The acoustic imaging system of claim 26, further comprising:

means for determining a depth of a feature within said target.

32. The acoustic imaging system of claim 26, wherein a portion of the acoustic beam transmitted through at least a portion of the target is received by the acoustic lens system.

33. The acoustic imaging system of claim 26, wherein a portion of the acoustic beam reflected from the target is received by the acoustic lens system.

* * * * *